(12) United States Patent
Cronin

(10) Patent No.: US 6,439,884 B1
(45) Date of Patent: Aug. 27, 2002

(54) DENTAL CAST TRAY ASSEMBLY

(76) Inventor: Richard J. Cronin, 45 Cypress St., Medfield, MA (US) 02052

( * ) Notice: Subject to any disclaimer, the term of this patent is extended or adjusted under 35 U.S.C. 154(b) by 0 days.

(21) Appl. No.: 09/772,264

(22) Filed: Jan. 29, 2001

Related U.S. Application Data

(63) Continuation-in-part of application No. 09/713,126, filed on Nov. 15, 2000.

(51) Int. Cl.[7] .............................................. A61C 19/00
(52) U.S. Cl. ......................................... 433/34; 433/60
(58) Field of Search ............................... 433/34, 74, 60

(56) References Cited

U.S. PATENT DOCUMENTS

| | | | |
|---|---|---|---|
| 3,702,027 A | * 11/1972 | Marshall et al. | 433/34 |
| 4,035,916 A | 7/1977 | Eveland | 433/60 |
| 4,139,943 A | 2/1979 | Dragan | |
| 4,265,619 A | 5/1981 | Lucki et al. | 433/54 |
| 4,363,625 A | 12/1982 | der Avanessian | 433/74 |
| 4,508,506 A | 4/1985 | Jackson | 433/74 |
| 4,608,016 A | 8/1986 | Zeiser | 433/74 |
| 4,767,330 A | 8/1988 | Burger | 433/213 |
| 4,898,359 A | 2/1990 | Gopon | 249/54 |
| 5,352,117 A | 10/1994 | Silva | 433/60 |
| 5,393,227 A | 2/1995 | Nooning | 433/74 |
| 5,506,095 A | 4/1996 | Callne | 433/34 |
| 6,106,284 A | 8/2000 | Cronin et al. | 433/34 |

FOREIGN PATENT DOCUMENTS

| GB | 2230958 | * 11/1990 | 433/49 |
|---|---|---|---|

* cited by examiner

Primary Examiner—Cary E. O'Connor
(74) Attorney, Agent, or Firm—Kreigsman & Kreigsman

(57) ABSTRACT

A dental cast tray assembly used to form a dental cast model comprises a base and a tray removably mounted on the base. The base includes a top surface which is recessed to form a support surface and a pair of restriction walls which protrude up from the support surface, each restriction wall including a plurality of surface irregularities. The base also includes an elongated, tubular projection which extends nearly the entire length of the base. The projection includes a rounded top, a pair of inwardly curved sidewalls and an elongated slot. The tray includes an elongated socket which includes a pair of thin fingers that are capable of flexion. The socket defines an opening into which the projection is capable of being releasably press-fit. The tray is notched to form first and second outer restriction walls, each outer restriction wall including a plurality of surface irregularities which are sized and shaped to engage the surface irregularities formed on the base.

16 Claims, 4 Drawing Sheets

DENTAL CAST TRAY ASSEMBLY

CROSS-REFERENCE TO RELATED APPLICATIONS

The present application is a continuation-in-part of U.S. patent application Ser. No. 09/713,126, inventor Richard J. Cronin, filed Nov. 15, 2000.

BACKGROUND OF THE INVENTION

The present invention relates generally to the dental industry and, more particularly, to dental tools which are used in the production of dental cast models.

In the dental industry, technicians commonly construct dental models. A dental model of the entire mouth of a patient typically comprises an upper jaw model and a lower jaw model which are affixed to one another by an articulator. An articulator is a device comprising upper and lower mounting platforms which are connected to the upper and lower jaw model elements. The articulator enables for centric, lateral and protrusive movement of the upper jaw model relative to the lower jaw model in order to closely simulate the relationships and the actual movement, or bite, of the mouth of the patient.

Various types of devices and procedures have been used in the art for creating dental models.

One method for manufacturing dental models which is well known and commonly used in the art involves molding the dental model using a casting material. Specifically, one or more impression trays are filled with rubber based impression material. Each impression tray is then urged into the mouth of the patient so as to create a negative impression of the teeth of the patient into the rubber based impression material. If necessary, excess impression material is trimmed from the impression tray after the negative impression is formed.

After the negative impression has been formed, the impression tray is typically transported to a dental laboratory where the dental cast model is manufactured. Specifically, the negative impression created in the impression tray is filled with a soft casting material, such as dental stone, plaster or epoxy. The impression tray is then inverted and mounted upon a pre-formed mounting device, such as a dental cast tray or base. After the casting material has had an opportunity to harden, the impression tray is removed so that the casting material forms a positive dental impression on the mounting surface.

Molded dental models are often used to manufacture crowns, bridges, inlays, dentures and other dental prosthetics outside of the mouth of the patient. The construction of dental prosthetics typically necessitates the ability to remove one or more individual model teeth from its spatial physical relationship relative to the remainder of the dental cast model for the purpose of constructing accurate margins and contours. In the event that two or more individual units of bridgework are to be joined, it is necessary that the working model segments be accurately and repeatedly returned to their original relationships precisely as they existed prior to any cutting, separations or disassembly of the model.

In order to effectively remove an individual model segment from the remainder of the dental model, the entire jaw model is typically removed from the mounting device and positioned upon a flat cutting surface, such as a table. A cutting device, such as a saw, can then be used to separate the desired model teeth from the remainder of the dental model. After the technician has completed manufacture of the dental work, the dental model can be re-assembled onto the mounting device.

It should be noted that during the re-assembly of the dental cast model, it is essential that precise registration and desired alignment be maintained between the working model segments and the remainder of the molded dental cast model.

In U.S. Pat. No. 5,393,227 to W. H. Nooning, there is disclosed a dental impression handling tool consisting of two base structures shaped to approximate two opposite quadrants of a full dental arch, and two similarly-shaped inserts that snap fit into the base structures. Each base includes a wide, upward facing trough approximating the placement and curvature of teeth within a dental quadrant. The upper surface of each insert is attached to a positive dental mold by means of protrusions that extend from the top horizontal surface of the insert, the protrusions being encased within the mold material. Positive positional relationship is maintained between each base and its mating insert by the use of an interlocking and non-recurring geometric pattern that is carried by the internal vertical walls of the trough in the base, and by a matching geometric pattern that is carried by the outer vertical walls of two vertically downward extending ribs on the underside of the insert. A second deeper, narrow and centrally located trough is formed in each base. This second trough mates with a third center rib that protrudes from the bottom surface of each insert. The insert's center rib contains a retainer bead along both vertical side walls. This bead provides a snap-lock fit into a corresponding negative indentation formed along the vertical side walls of the center trough of in each base. The center rib in each insert contains cylindrical cavities which allow the insertion of standard dental dowels or suitable substitutes.

Dental impression handling tools of the type described above in Nooning have been found to be experience numerous drawbacks As a first drawback, dental impression handling tools of the type described above in Nooning are undesirable in that the base comprises an elongated slot into which debris, such as plaster, can collect. As a result, it has been found that the insert is often unable to secure a proper fit within the base structure, thereby precluding proper alignment, which is highly undesirable.

As a second drawback, dental impression handling tools of the type described in Nooning are undesirable in that the bottom surface of the each insert includes various sized ribs, thereby creating a bottom surface which is highly unstable. As a result, when the insert is placed upon a laboratory table in order to cut the desired model teeth from the remainder of the dental cast model, the non-flat and unstable nature of the bottom surface of each insert renders the cutting process extremely difficult, which is highly undesirable.

Accordingly, in U.S. Pat. No. 6,106,284 to R. J. Cronin et al., there is disclosed, in one embodiment, a dental cast tray assembly used to form a dental cast model which comprises a base and a tray removably mounted on the base. The base includes a top surface, a flat bottom surface, a front wall, a rear wall and a plurality of projections formed on its top surface in a non-recurring, random pattern. Each of the plurality of projections is generally cylindrically-shaped and includes a convex free end. The tray includes a top surface adapted to support the dental cast model, a flat bottom surface, a front wall, a rear wall, a retention bar formed on its top surface and a plurality of openings formed in its bottom surface in the same non-recurring, random pattern in which the plurality of projections are disposed on the base. Each of the plurality of openings is defined by four sidewalls and is generally hourglass shaped in lateral cross-section. Two of the four sidewalls which define each of the plurality of openings include an elongated rib. In use, the tray is mounted on the base such that the bottom surface of the tray abuts against the top surface of the base and so that the front wall of the tray is flush with the front wall of the base. With the tray mounted on the base, one projection in the base projects into an associated opening in the tray, the elongated ribs serving to retain each projection within its associated opening with limited retention.

Although highly effective in constructing a dental cast model, the dental cast tray assembly described in Cronin et al. suffers from some notable drawbacks.

As a first drawback, it has been found that the dental cast tray assembly described in Cronin et al. is difficult to manufacture due to the T-shape of the retainer bar. Specifically, the undercuts of the T-shaped retainer bar are difficult to create using conventional molding processes, thereby increasing the overall cost to manufacture the dental cast tray assembly, which is undesirable.

As a second drawback, it has been found that the dental cast tray assembly described in Cronin et al. is difficult to manufacture due to the particular arrangement of posts on the base and openings in the tray. Specifically, the exactness required in constructing each of the plurality of posts on the base to fit snugly within an associated opening in the tray significantly complicates the molding process, thereby increasing the overall cost to manufacture the dental cast tray assembly, which is undesirable.

As a third drawback, it has been found that the dental cast tray assembly described in Cronin et al. often requires considerable clean-up. Specifically, in use, casting material is spread both within the negative impression of the impression tray and onto the top surface of the tray around the retention bar. However, it has been found that, before the casting material has had a chance to harden, some of the casting material often drips off of the top surface of the tray and onto the base and working table. As a result, the dental technician is often required to spend a considerable amount of time and energy to clean-up the excess casting material which accumulates on the base and the working surface, which is undesirable.

As a fourth drawback, it has been found that the dental cast tray assembly described in Cronin et al. is often difficult to use. Specifically, in use, casting material is spread both within the negative impression of the impression tray and onto the top surface of the tray around the retention bar. However, it has been found that the application of the casting material around the entire retention bar is often difficult to achieve due to the undercuts of the T-shaped retention bar. As a result, if the casting material is not properly spread around the entire retaining bar, air gaps can form between the plaster and the tray, thereby weakening the strength of the retention of the dental cast model on the tray, which is undesirable.

As a fifth drawback, it has been found that the tray and base of the dental cast tray assembly described in Cronin et al. are difficult to mount together. Specifically, each of the large quantity of posts on the base must be properly aligned and inserted into an associated opening in the tray. As a result, a considerable amount of dexterity is required to ensure that each post projects within an associated opening, which is undesirable. In addition, due to the large quantity of posts and openings, a considerable amount of retentive force must be overcome in order to advance each post into its associated opening, which is undesirable.

As a sixth drawback, it has been found that the tray and base of the dental cast tray assembly described in Cronin et al. are difficult to separate. Specifically, the large number of posts and openings creates a significant retentive force between the base and the tray which is difficult to overcome, which is undesirable. Furthermore, because the tray lies flush on top of the base, the user is incapable of wedging an object between the base and the tray to facilitate separation, which is undesirable.

As a seventh drawback, it has been found that the dental cast tray assembly described in Cronin et al. does not indicate to the user whether the tray is adequately mounted onto the base. Specifically, the user is often unaware if the tray has been properly mounted on the base such that each projection extends completely into its associated openings, which is undesirable.

SUMMARY OF THE INVENTION

It is an object of the present invention to provide a new and improved dental cast tray assembly which can be used to produce a dental cast model.

It is another object of the present invention to provide a dental cast tray assembly as described above which includes a tray on which the dental cast model is mounted.

It is yet another object of the present invention to provide a dental cast tray assembly as described above which allows for repeated removal and replacement of the tray onto a base with proper alignment.

It is still another object of the present invention to provide a dental cast tray assembly as described above which enables the dental cast model to be easily cut into working segments.

It is another object of the present invention to provide a dental cast tray assembly as described above wherein the tray is constructed to securely retain the dental cast model thereon.

It is still another object of the present invention to provide a dental cast tray assembly as described above which is inexpensive to manufacture, has a minimal number of parts, is limited in size and can be very easily used.

Accordingly, as one feature of the present invention, there is provided a dental cast tray assembly for forming a dental cast model, comprising a base having an elongated projection, and a tray removably mounted on said base, said tray being adapted to support the dental cast model, said tray including an elongated opening, wherein said projection is sized and shaped to releasably fit into the opening in said tray.

As another feature of the present invention, there is provided a dental cast tray assembly for forming a dental cast model, comprising a base, and a tray removably mounted on said base, said tray being adapted to support the dental cast model, wherein, with said tray mounted on said base, said dental cast tray assembly is shaped to include a slot at the junction between said base and said tray for assisting in the removal of said tray from said base.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration an embodiment for practicing the invention. The embodiment will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the present invention and, together with the description, serve to explain the principles of the invention. In the drawings wherein like reference numerals represent like parts.

DETAILED DESCRIPTION OF A PREFERRED EMBODIMENT

Figure 1:
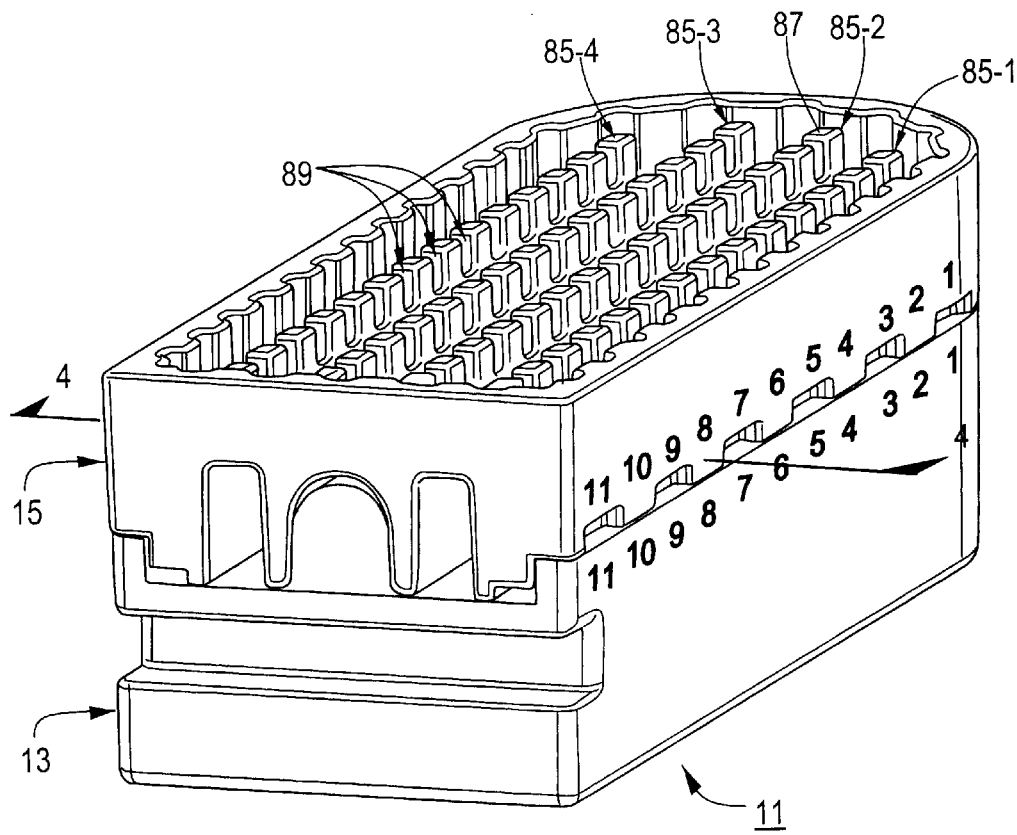
FIG. 1 is a top perspective view of a dental cast tray assembly constructed according to the teachings of the present invention, the dental cast tray assembly being shown with the tray mounted on the base.

Referring now to FIGS. 1–4, there is shown a dental cast tray assembly constructed according to the teachings of the present invention, the dental cast tray assembly being represented generally by reference numeral 11. As will be described further in detail below, dental cast tray assembly 11 can be used to form a dental cast model 12.

It should be noted that dental cast tray assembly 11 is shaped to approximate a straight, or universal, quadrant of a full dental arch. As a result, dental cast tray assembly 11 is preferred when forming a dental cast model for a limited number of teeth, such as a single molar. Because dental cast tray assembly 11 utilizes a limited amount of casting material when forming a dental cast model, dental cast tray assembly 11 can provide considerable cost savings over larger sized dental cast tray assemblies, which is highly desirable.

It should also be noted that dental cast tray assembly 11 is not limited to being shaped to approximate a straight quadrant of a full dental arch. Rather, it is to be understood that dental cast tray assembly 11 could be alternatively shaped without departing from the spirit of the present invention. For example, dental cast tray assembly 11 could be shaped to approximate a full dental arch without departing from the spirit of the present invention. As can be appreciated, if shaped to approximate a full dental arch, dental cast tray assembly 11 could be used to form a dental cast model 12 for either the upper jaw or the lower jaw of a patient. Accordingly, an upper jaw cast model and a lower jaw cast model can be supported by an articulator to create a positive dental cast model of the entire mouth of a patient which can then be used in the dental industry to manufacture crowns, bridges or other dental prosthetics.

Dental cast tray assembly 11 comprises a base 13 and a tray 15 removably mounted on base 13. Both base 13 and tray 15 are made of a plastic material which retains its rigidity in thin-wall construction and which is able to be easily manually cut by a saw blade. Preferably, base 13 is manufactured of an ABS plastic material and tray 15 is manufactured of a 20% glass-filled polycarbonate material.

Preferably, each of base 13 and tray 15 is formed as an integral piece using conventional molding techniques. However, it is to be understood that base 13 and tray 15 are not limited to being formed using conventional molding techniques. Rather, base 13 and tray 15 could be constructed using alternative conventional manufacturing techniques without departing from the spirit of the present invention.

Figure 2:
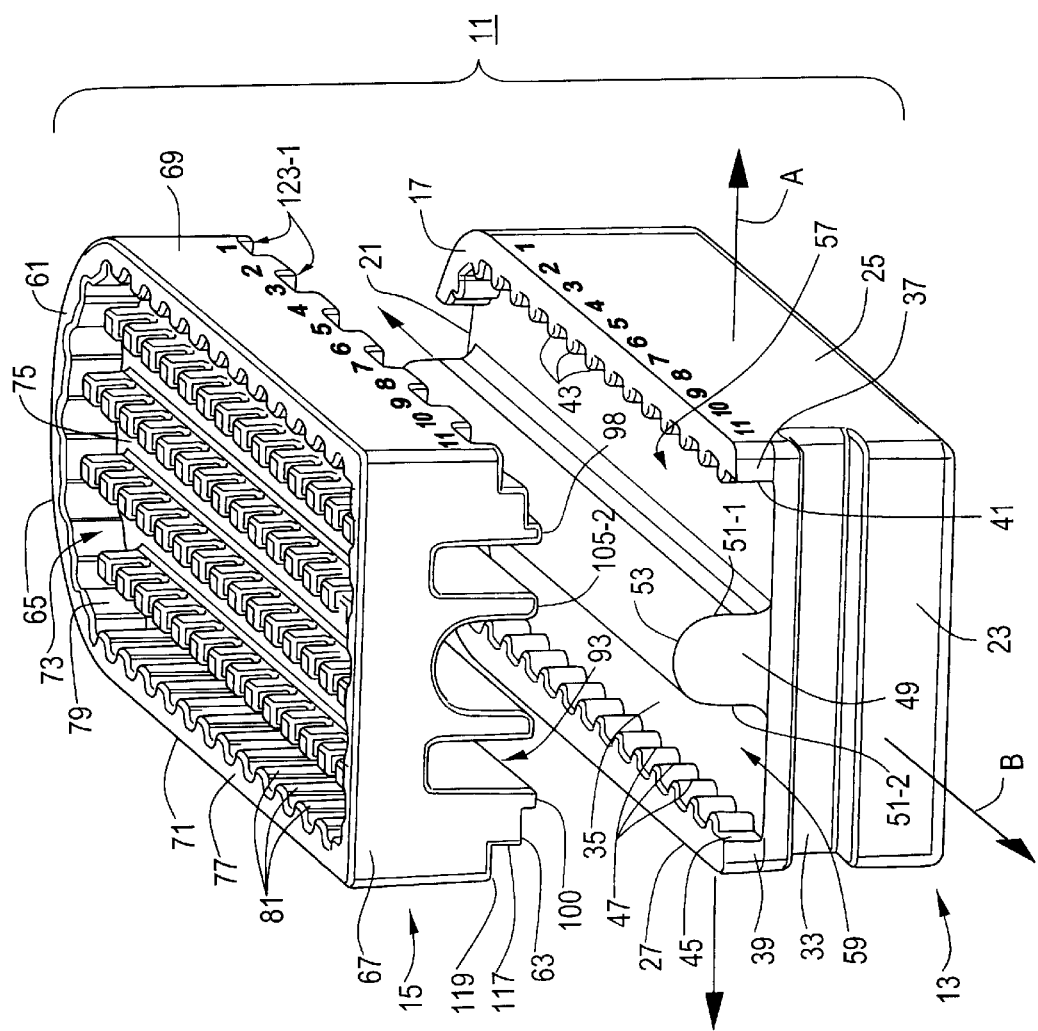
FIG. 2 is a top pop perspective view of the dental cast tray assembly shown in FIG. 1, the dental cast tray assembly being shown with the tray separated from the base.
Figure 3:
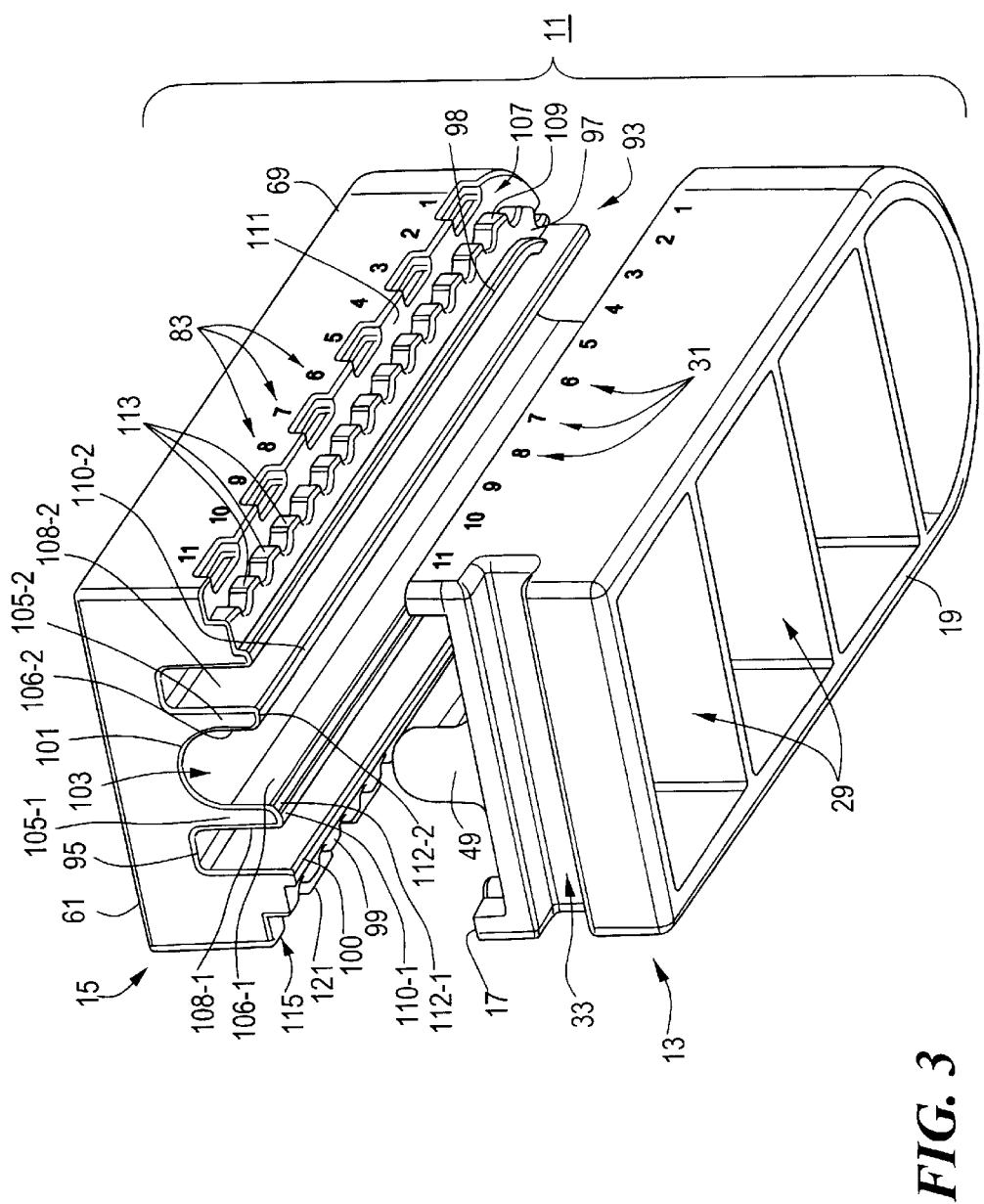
FIG. 3 is a bottom perspective view of the dental cast tray assembly shown in FIG. 2, the dental cast tray assembly being shown with the tray separated from the base.

Referring now to FIGS. 2–3, base 13 comprises a top surface 17, a bottom surface 19, a front wall 21, a rear wall 23, a first sidewall 25 and a second sidewall 27.

Bottom surface 19 is shaped to include a plurality of square-shaped recesses 29 in order to reduce the amount of plastic material required to manufacture base 13. It should be noted that bottom surface 19 is generally flat so as to enable base 13 to be placed on a working surface in a stable position, which is highly desirable.

Alignment indicia 31 are provided on sidewalls 25 and 27 of base 13. As will be described further in detail below, alignment indicia 31 provide a visible guide for ensuring proper alignment between tray 15 and base 13, as shown in FIG. 1. Preferably, alignment indicia 31 are in the form of sequential numbering. However, it is to be understood that any types of alignment indicia, such as alphabetical or symbolic designations, could be provided on sidewalls 25 and 27 of base 13 without departing from the spirit of the present invention.

Rear wall 23 is generally flat and is shaped to include an elongated slot 33. Elongated slot 33 is sized and shaped to receive a hinge for an articulator. As such, a pair of dental cast tray assemblies 11 can be supported by an articulator to create a positive dental cast model of a portion of the mouth of a patient, wherein an upper dental cast tray assembly is capable of centric, lateral and protrusive movement relative to a lower dental cast tray assembly.

It should be noted that elongated slot 33 is formed along the entire length of rear wall 23, from first sidewall 25 to second sidewall 27, in order to facilitate the installation of a hinge for an articulator therein. Specifically, the hinge of an articulator can easily be slid into elongated slot 33, from either side, to create a positive dental cast model for the entire mouth of a patient.

Top surface 17 of base 13 is recessed so as to form a substantially flat support surface 35 between top surface 17 and bottom surface 19, a first restriction wall 37 which projects up from support surface 35 and a second restriction wall 39 which projects up from support surface 35.

First restriction wall 37 includes an inner surface 41 which is shaped to include a plurality of arcuate ribs 43. Similarly, second restriction wall 39 includes an inner surface 45 which is shaped to include a plurality of arcuate ribs 47. It should be noted that first and second restriction walls 37 and 39 are not limited to including arcuate ribs 43 and 47, respectively. Rather, it is to be understood that first and second restriction walls 37 and 39 could include alternative types of surface irregularities, such as ratchet teeth, in place of arcuate ribs 43 and 47, respectively, without departing from the spirit of the present invention.

An elongated projection 49 is integrally formed onto support surface 35 of base 13 and extends approximately the entire length of base 13 from front wall 21 to rear wall 23. Projection 49 is generally in the form of an elongated tube and comprises a first and second sidewalls 51-1 and 51-2 and a rounded top, or head, 53. Sidewalls 51 are integrally formed onto support surface 35 and bow slightly inward. Top 53 is integrally formed onto the free ends of sidewalls 51 and curves outward.

Figure 4:
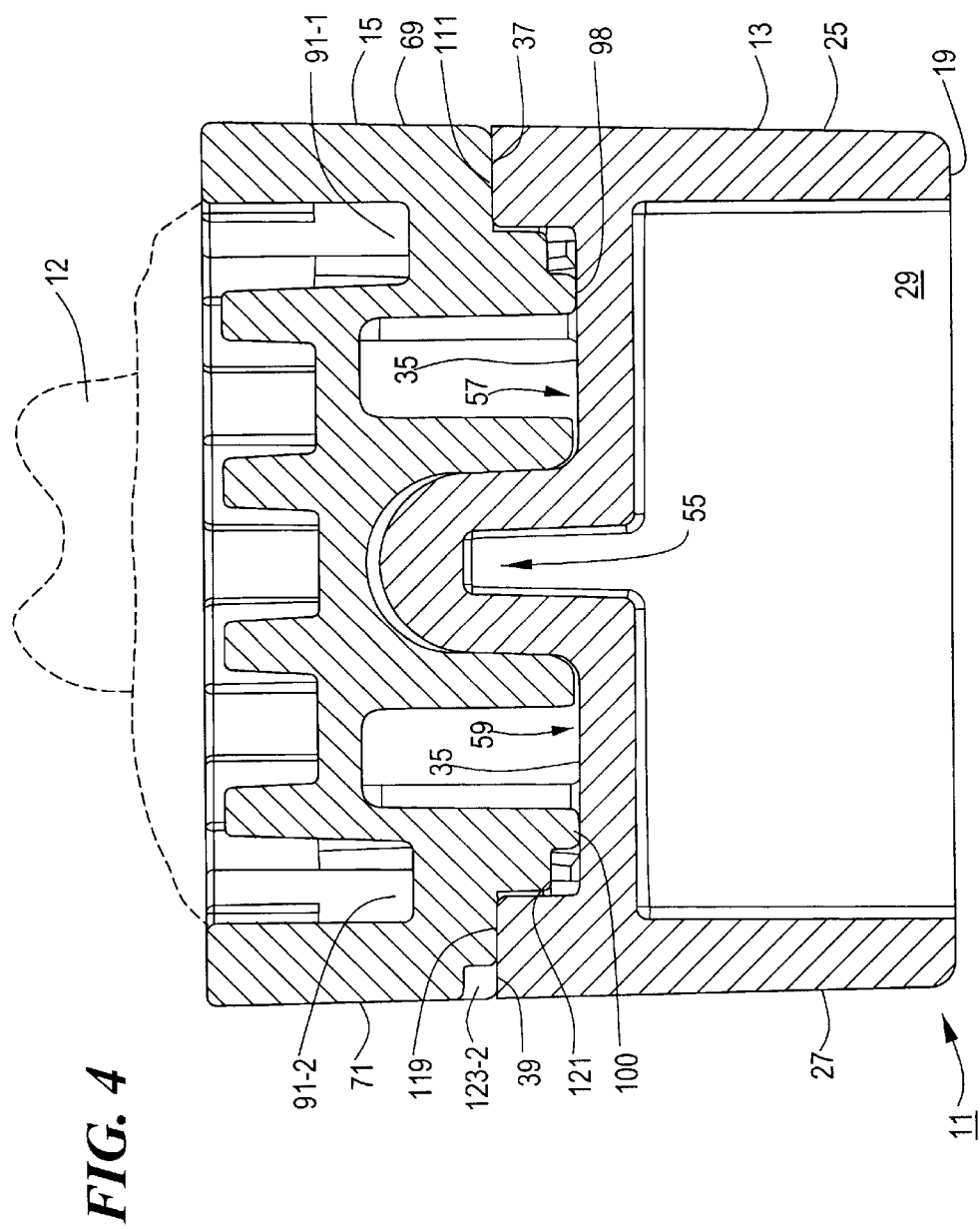
FIG. 4 is a section view of the dental cast tray assembly shown in FIG. 1, taken along lines 4—4, the dental cast tray assembly being shown with a positive dental cast model formed on the tray, the positive dental cast model being shown in phantom.

Projection 49 is shaped to include an elongated, longitudinal slot 55. Specifically, projection 49 is cored so as to form slot 55 which extends along the length of projection 49 and which is generally U-shaped in lateral cross-section, as shown in FIG. 4. Although projection 49 is shown being cored so as to form slot 55, it should be noted that slot 55 could alternatively be formed into the outer surface of rounded top 53 without departing from the spirit of the present invention.

It should be noted that coring projection 49 so as to form elongated slot 55 provides three principal advantages.

As a first advantage, coring projection 49 so as to form elongated slot 55 enables projection 49 to be inwardly compressible, thereby allowing for a temporary reduction in the lateral cross-sectional area of projection 49. As a result, the inward compressibility of projection 49 enables projection 49 to be press-fit within an associated socket, as will be described further in detail below.

As a second advantage, coring projection 49 so as to form elongated slot 55 serves to simplify the process for molding dental cast tray assembly 11. Specifically, coring projection 49 reduces the amount of material needed to construct projection 49, thereby reducing molding costs and preventing molding distortion.

As a third advantage, coring projection 49 so as to form elongated slot 55, rather than forming the elongated slot into the outer surface of rounded top 53, eliminates the possibility of debris falling into slot 55.

Projection 49 extends along the length of base 13 at the approximate mid-point between first restriction wall 37 and second restriction wall 39. As a result, support surface 35, restriction wall 37 and projection 49 together partially define a first recess portion 57. Similarly, support surface 35, restriction wall 39 and projection 49 together partially define a second recess portion 59.

Tray 15 comprises a top surface 61, a bottom surface 63, a front wall 65, a rear wall 67, a first sidewall 69 and a second sidewall 71.

Top surface 61 of tray 15 is recessed so as to form an enclosed reservoir 73 for holding the casting material which is used to create dental cast model 12. Specifically, top surface 61 of tray 15 is recessed to form a substantially flat support surface 75 between top surface 61 and bottom surface 63. Top surface 61 of tray 15 is recessed to also form a retention wall 77 which projects up from support surface 75 to top surface 61. Together, support surface 75 and retention wall 77 define enclosed reservoir 73.

It should be noted that retention wall 77 protrudes up from support surface 75 to top surface 61 along the entire outer periphery of support surface 75. In this manner, retention wall 77 serves as a wall for completely enclosing reservoir 73. As will be described further in detail below, entirely enclosing reservoir 73 serves to retain the casting material deposited therewithin during the dental model construction process, thereby preventing the casting material from spilling outside of reservoir 73 and onto front wall 65, rear wall 67, sidewalls 69 and 71 and/or base 13.

Retention wall 77 includes an inner surface 79 which is shaped to include a plurality of teeth 81 for retaining dental cast model 12 within reservoir 73. Teeth 81 are generally arcuate and protrude into reservoir 73. However, it should be noted that inner surface 79 of retention wall 77 is not limited to including a plurality of generally arcuate teeth 81. Rather, it is to be understood that inner surface 79 of retention wall 77 could include alternative types of surface irregularities, such as V-shaped teeth, in place of arcuate teeth 81 in order to retain dental cast model 12 within reservoir 73 without departing from the spirit of the present invention.

Alignment indicia 83 are provided on sidewalls 69 and 71 of tray 15. Alignment indicia 83 provide a visible guide for ensuring proper alignment between tray 15 and base 13 when tray 15 is mounted onto base 13. Specifically, as tray 15 is being mounted onto base 13, the user is able to visibly compare the position of indicia 83 on tray 15 relative to indicia 31 on base 13 in order to ensure that tray 15 is mounted on base 13 in proper alignment therewith, as shown in FIG. 1. Preferably, alignment indicia 83 are in the form of sequential numbering. However, it is to be understood that any types of matching alignment indicia, such as alphabetical or symbolic designation, could be provided on base 13 and tray 15 of dental cast tray assembly 11 without departing from the spirit of the present invention.

Four elongated retention bars 85-1 through 85-4 are formed onto support surface 75 and project into reservoir 73, each retention bar 85 being generally rectangular in lateral cross-section. Retention bars 85 are disposed to extend along the length of tray 15 within reservoir 73 in a substantially parallel, spaced apart relationship. As will be described further in detail below, retention bars 85 assist in retaining of dental cast model 12 within reservoir 73.

It should be noted that tray 15 is not limited to the use of elongated, parallel, spaced apart, retention bars 85 to retain dental cast model 12 within reservoir 73. Rather, it is to be understood that any suitable size, shape or number of projections could be formed on support surface 75 of tray 15 in order to retain dental cast model 12 within reservoir 73 without departing from the spirit of the present invention. For example, a plurality of cylindrical, rectangular or X-shaped posts in lateral cross-section could be formed on support surface 75 of tray 15 in place of retention bars 85 without departing from the spirit of the present invention.

Each retention bar 85 protrudes up from support surface 75 a height which is slightly less than the height which retention wall 77 protrudes up from support surface 75. Each retention bar 85 is shaped to include a substantially flat top surface 87 and a plurality of recesses 89 formed in top surface 87. Each recess 89 is generally rectangular in shape and extends down from top surface 87. Together, retention bars 85 and recesses 89 assist in retaining dental cast model 12 within reservoir 73.

A pair of retention channels 91 are formed into support surface 75, as shown in FIG. 4. Specifically, a first retention channel 91-1 is formed into support surface 75 between retention bar 85-1 and sidewall 69 and a second retention channel 91-2 is formed into support surface 75 between retention bar 85-4 and sidewall 71.

It should be noted that retention channels 91 are preferably formed as elongated channels to facilitate the process for molding tray 15. However, However, it is to be understood that retention channels 91 could be alternatively sized and shaped without departing from the spirit of the present invention. As an example, retention openings 91 could be in the form of a plurality of cylindrical or rectangular holes formed into support surface 75 without departing from the spirit of the present invention.

Bottom surface 63 of tray 15 includes an elongated central recess 93 which defines a support surface 95 between bottom surface 63 and top surface 61. Elongated central recess 93 also defines a first projection 97 and a second projection 99, projections 97 and 99 being disposed on opposite sides of central recess 93. First projection 97 is shaped to include a foot 98 and second projection 99 is shaped to include a foot 100.

It should be noted that first projection 97 has a longitudinal cross-sectional area which is less than the longitudinal cross-sectional area of first recess portion 57. Similarly, it should be noted that second projection 99 has a longitudinal cross-sectional area which is less than the longitudinal cross-sectional area of the second recess portion 59.

An elongated socket 101 is formed into tray 15 along elongated central recess 93, socket 101 extending approximately the entire length of tray 15 from front wall 65 to rear wall 67. Socket 101 is shaped to define an elongated opening 103 which is generally U-shaped in lateral cross-section.

It should be noted that socket 101 is sized and shaped so that projection 49 can be press-fit into opening 103, with the lateral cross-sectional area of projection 49 being slightly less than the lateral cross-sectional area of opening 103. As such, dental cast tray assembly 11 is capable of being disposed between an unlocked position in which tray 15 is separated from base 13 and a locked position in which tray 15 is mounted onto base 13 with projection 49 fittingly disposed within opening 103 to secure tray 15 onto base 13, as will be described further in detail below.

Socket 101 includes a first elongated finger 105-1 which protrudes out from support surface 95 along approximately the entire length of tray 15 from front wall 65 to rear wall 67. Similarly, socket 101 includes a second elongated finger 105-2 which protrudes out from support surface 95 along approximately the entire length of tray 15 from front wall 65 to rear wall 67.

Finger 105-1 comprises an inner surface 106-1, an outer surface 108-1 and a free end 110-1. Finger 105-1 further comprises a beveled surface 112-1 at the junction of inner surface 106-1 and free end 110-1. Similarly, finger 105-2 comprises an inner surface 106-2, an outer surface 108-2 and a free end 110-2. Finger 105-2 further comprises a beveled surface 112-2 at the junction of inner surface 106-2 and free end 110-2. As can be appreciated, beveled surfaces 112 serve to facilitate mounting tray 15 on base 13.

It should be noted that each finger 105 has a relatively thin lateral cross-sectional area. As a result of their relatively thin construction, fingers 105 are capable of limited flexion, thereby enabling fingers 105 to slightly flex outward as projection 49 is press-fit into socket 101, as will be described further in detail below.

A first elongated notch 107 is formed into bottom surface 63 of first contact projection 97 along first sidewall 69. Notch 107 is generally rectangular in lateral cross-section and serves to create an outer restriction wall 109 in first contact projection 97 and an abutment surface 111. Outer restriction wall 109 is shaped to include a plurality of arcuate ribs 113.

Similarly, a second elongated notch 115 is formed into bottom surface 63 of second contact projection 99 along second sidewall 71. Notch 115 is generally rectangular in lateral cross-section and serves to create an outer restriction wall 117 in second contact projection 99 and an abutment surface 119. Outer restriction wall 117 is shaped to include a plurality of arcuate ribs 121.

It should be noted that ribs 113 and 121 on tray 15 are sized and shaped to matingly engage ribs 43 and 47, respectively, on base 13. As a consequence, the abutment of restriction walls 109 and 117 on tray 15 against restriction walls 37 and 39, respectively, on base 13 serves to prevent movement of tray 15 along the lateral axis, as represented by arrow A in FIG. 2, relative to base 13 when dental cast tray assembly 11 is in its locked position. In addition, the engagement of ribs 113 and 121 on tray 15 with ribs 43 and 47, respectively, on base 13 serves to prevent movement of tray 15 along the longitudinal axis, as represented by arrow B in FIG. 2, relative to base 13 when dental cast tray assembly 11 is in its locked position. Accordingly, with dental cast tray assembly 11 disposed in its locked position, tray 15 remains fixed in its position relative to base 13, which is highly desirable.

A plurality of spaced apart slots 123-1 are formed in sidewall 69 along abutment surface 111. Similarly, a plurality of spaced apart slots 123-2 are formed in sidewall 71 along abutment surface 119. Each slot 123 is generally square shaped in lateral cross-section and rectangular shaped in longitudinal cross-section. As can be appreciated, with dental cast tray assembly 11 disposed in its locked position with tray 15 mounted onto base 13, slots 123 facilitate the removal of tray 15 from off of base 13. Specifically, slots 123 enable a flat device, such as a knife blade or a flat head screwdriver, to be wedged between tray 15 and base 13 to facilitate the removal of tray 15 from off of base 13, which is highly desirable.

Preferably, each slot 123-2 is disposed to align between successive slots 123-1. As a result, if tray 15 is cut into a small working fragment, the user is ensured that at least one of slots 123-1 or one of slots 123-2 remains present on small fragment, which is highly desirable.

It should be noted that dental cast tray assembly 11 is not limited to the number of slots 123 in sidewalls 69 and 71 shown in the drawings in order to facilitate the separation of tray 15 from base 13 when dental cast tray assembly 11 is in its locked position. Rather, it is to be understood that a different number (i.e., as few as one) or shape (i.e., arcuate) of slots could be formed into sidewall 69 and/or sidewall 71 in order to assist in the removal of tray 15 from base 13 without departing from the spirit of the present invention. Furthermore, it is to be understood that slots 123 could be formed into sidewall 25 and/or sidewall 27 of base 13 along top surface 17, rather than being formed into tray 15, in order to facilitate the separation of tray 15 from base 13 when dental cast tray assembly 11 is in its locked position without departing from the spirit of the present invention.

In use, dental cast tray assembly 11 can be used to manufacture dental cast model 12 in the following manner. Dental cast tray assembly 11 is initially configured in its locked position with tray 15 mounted onto base 13. Specifically, tray 15 is mounted onto base 13 such that projection 49 is fittingly disposed within opening 103 in socket 101. With dental cast tray assembly 11 disposed in its locked position, as shown in FIG. 4, bottom surface 63 of foot 98 abuts against support surface 35 within first recess portion 57, bottom surface 63 of foot 100 abuts against support surface 35 within second recess portion 59, abutment surface 111 contacts top surface 17 of first restriction wall 37 and abutment surface 119 contacts top surface 17 of second restriction wall 39 so that tray 15 lies flush on top of base 13. In addition, with dental cast tray assembly 11 disposed in its locked position, sidewall 69 lies flush with sidewall 25, sidewall 71 lies flush with sidewall 27, front wall 65 lies flush with front wall 21 and rear wall 67 lies flush with rear wall 23. Accuracy in the positional relationship between tray 15 and base 13 is maintained by the engagement of ribs 113 and 121 with ribs 43 and 47, respectively, and through visual inspection of the alignment between indicia 83 and indicia 31.

It should be noted that tray 15 mounts onto base 13 using a press-fit arrangement. Specifically, with tray 15 dismounted from base 13, projection 49 on base 13 is disengaged from socket 101 of tray 15. As tray 15 is advanced towards base 13 for mounting, rounded top 53 of projection 49 is guided into socket 101 by beveled surfaces 112 of fingers 105. As top 53 begins to project into socket 101, projection 49 slightly inwardly compresses and fingers 105 outwardly flex, or give, so as to enable projection 49 to fit between fingers 105. Once projection 49 is urged completely between fingers 105 and into socket 101, projection 49 resiliently expands to its original shape and fingers 105 resiliently collapse inward to their original position so that inner surfaces 106 of fingers 105 contact against inwardly bowed sidewalls 51 and 52 of projection 49, thereby securing dental cast tray assembly 11 in its locked position with tray 15 mounted on base 13. As can be appreciated, once projection 49 is positioned entirely within socket 101 so as to configure dental cast tray assembly 11 in its locked position, dental cast tray assembly 11 produces a tactile locking sensation, thereby notifying the user that dental cast tray assembly 11 is properly disposed in its locked position, which is a principal feature of the present invention.

It should also be noted that the implementation of a single elongated projection 49 and a corresponding single elongated socket 101 in dental cast tray assembly 11 facilitates the process of mounting tray 15 onto base 13 and dismounting tray 15 from base 13. Specifically, because the user is required to dispose a single projection 49 within a single socket 101, the process of aligning tray 15 onto base 13 during the mounting process is relatively simple and easy, which is a principal object of the present invention. Furthermore, because the user is required to dispose a single projection 49 within a single socket 101, the amount of force required to mount tray 15 onto base 13 and/or remove tray 15 from base 13 is limited, which is also a principal object of the present invention.

It should further be noted that the use of a single elongated projection 49 and a single elongated socket 101 greatly simplifies the tooling process for manufacturing dental cast tray assembly 11. As a result, dental cast tray assembly 11 is relatively inexpensive to manufacture, which is a principal object of the present invention.

With dental cast tray assembly 11 disposed in its locked position with tray 15 mounted on base 13, an impression tray filled with a rubber based material is used to take a negative impression of selected teeth of a patient. If necessary, excess rubber based material is trimmed from the impression tray after the impression has been taken.

The negative impression is then transported to a dental laboratory where dental cast model 12 is manufactured. Specifically, a thick casting material, such as plaster, is deposited within the negative impression. At the same time, the thick plaster is deposited within the entire enclosed reservoir 73 of tray 15 using a laboratory utensil. It should be noted that the plaster is deposited into the entire reservoir 73 from support surface 75 to top surface 61. As such, the plaster fills retention openings 91 and recesses 89 and covers teeth 81 and retention bars 85.

It should be noted that, because reservoir 73 is entirely enclosed by retention wall 73, the thick plaster can be easily deposited and contained therewithin, which is highly desirable. As a result, dental cast tray assembly 11 is exceptionally easy to use and requires minimal clean-up, which is highly desirable.

With the plaster material deposited into the negative impression and into reservoir 73 of tray 15, the filled negative impression is then flipped over onto top surface 61 of tray 15 and is maintained in a stable position, thereby enabling the plaster in the negative impression and the plaster in reservoir 73 to mix together.

After the plaster material hardens approximately ½ hour later, the rubber impression is peeled off tray 15, thereby leaving positive plaster cast model 12. It should be noted that plaster cast model 12 is securely attached to tray 15 by the hardening of the mold material of model 12 onto retention bars 85 and inner surface 79 of retention wall 77 and into retention openings 91 and recesses 89. Dental cast model 12 can then be used in the dental industry to manufacture crowns, bridges or other dental prosthetics.

Construction of a particular dental prosthetic begins by dismounting tray 15 from base 13. The separation of tray 15 from base 13 can be accomplished by inserting a flat device, such as a knife blade or flat head screwdriver, into one of slots 123 and using the flat device as a wedge to urge tray 15 off base 13. As can be appreciated, due to the limited retention of single head 53 within single socket 101, tray 15 can be removed from base 13 with a limited amount of force. After dismounting tray 15 from base 13, tray 15 is placed upon a flat cutting surface. Because bottom surface 63 of tray 15 is substantially flat, tray 15 is stable when positioned upon the cutting surface.

With tray 15 positioned on the cutting surface, construction of the dental prosthetic requires isolation of the tooth or teeth for which the prosthesis will be constructed from the remaining teeth. This is accomplished by sawing down through dental cast model 12 and tray 15 on both sides of the teeth which will receive the prosthesis. Once the appropriate saw cuts have been made, the section of teeth which was isolated is removed to allow ease of manipulation during construction of the prosthesis.

Upon completion of the prosthesis, tray 15, which supports the isolated teeth as well as the remaining untreated teeth, is remounted onto base 13 in the exact alignment prior to cutting. It should be noted that tray 15 is remounted onto base in the exact alignment prior to cutting due to the engagement of ribs 113 and 121 with ribs 43 and 47, respectively, and due to the visual alignment of indicia 22 with indicia 38. With tray 15 properly remounted back onto base 13, the dental technician is able to sufficiently inspect the precise relation of the prosthesis relative to the entire dental cast model 12.

The embodiment of the present invention described above is intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A dental cast tray assembly for forming a dental cast model, comprising:
   (a) a base having an elongated projection, and
   (b) a tray removably mounted on said base, said tray being adapted to support the dental cast model, said tray including a substantially flat bottom surface and an elongated opening, the bottom surface of said tray including an elongated socket which is sized and shaped to define the opening, said socket comprising a pair of fingers which are capable of flexion, (c) wherein said projection is sized and shaped to releasably fit into the opening in said tray.

2. The dental cast tray assembly of claim 1 wherein said projection is sized and shaped to be releasably press-fit into the opening in said tray.

3. The dental cast tray assembly of claim 1 wherein the elongated projection extends approximately the entire length of said base.

4. The dental cast tray assembly of claim 1 wherein the bottom surface of said tray includes a pair of feet.

5. The dental cast tray assembly of claim 1 wherein the elongated socket extends a substantial length of said base.

6. The dental cast tray assembly of claim 1 wherein the elongated socket extends approximately the entire length of said base.

7. The dental cast tray assembly of claim 1 wherein said base comprises a top surface which is recessed to form a support surface, a first restriction wall which protrudes up from the support surface and a second restriction wall which protrudes up from the support surface.

8. The dental cast tray assembly of claim 7 wherein the inner surface of the first restriction wall and the inner surface of the second restriction wall each include a plurality of surface irregularities.

9. The dental cast tray assembly of claim 8 wherein said tray is notched so as to form first and second outer restriction walls, the first outer restriction wall including a plurality of surface irregularities which are sized and shaped to matingly engage with the surface irregularities on the first restriction wall on said base when said tray is mounted on said base and the second outer restriction wall on said tray includes a plurality of surface irregularities which are sized and shaped to matingly engage with the surface irregularities on the second restriction wall on said base when said tray is mounted on said base.

10. The dental cast tray assembly of claim 1 wherein each of the pair of fingers includes an outer surface, an inner surface, a free end and a beveled surface at the junction of the inner surface and the free end.

11. The dental cast tray assembly of claim 1 wherein the bottom surface of said tray is shaped to define an elongated central recess, the socket being formed in the tray within the recess.

12. A dental cast tray for forming a dental cast tray model, comprising:

(a) a base comprising a top surface, and (b) a tray comprising a bottom surface, said tray being adapted to support the dental cast model, (c) wherein said tray is capable of being mounted onto said base so that the bottom surface of said tray contacts the surface of said base, at least one of the bottom surface of the tray and the top surface of the base including a slot for assisting in the removal of said tray from said base.

13. A dental cast tray assembly for forming a dental cast model, comprising:

(a) a base having an elongated projection which extends a substantial length of the base, said elongated projection being in the form of an elongated tube, and (b) a tray removably mounted on said base, said tray being adapted to support the dental cast model, said tray including an elongated opening, (c) wherein said projection is sized and shaped to releasably fit into the opening in said tray.

14. The dental cast tray assembly of claim 13 wherein the projection comprises a rounded top and a pair of inwardly curved sidewalls.

15. A dental cast tray assembly for forming a dental cast model, comprising:

(a) a base having an elongated projection which extends a substantial length of the base, wherein said projection is capable of being compressed, and (b) a tray removably mounted on said base, said tray being adapted to support the dental cast model, said tray including an elongated opening, (c) wherein said projection is sized and shaped to releasably fit into the opening in said tray.

16. A dental cast tray assembly for forming a dental cast model, comprising:

(a) a base having an elongated projection which extends a substantial length of the base, wherein said projection is shaped to include an elongated slot, and (b) a tray removably mounted on said base, said tray being adapted to support the dental cast model, said tray including an elongated opening, (c) wherein said projection is sized and shaped to releasably fit into the opening in said tray.

* * * * *